United States Patent [19]

Ferer et al.

[11] Patent Number: 5,264,906
[45] Date of Patent: Nov. 23, 1993

[54] BIOLUMINESCENCE BATHYPHOTOMETER

[75] Inventors: Kenneth M. Ferer, Covington, La.; James F. Case, Santa Barbara, Calif.; Edith A. Widder, Fort Pierre, Fla.; Steven A. Bernstein, Los Orias, Calif.; Mark Lowenstine, Denfield, Canada

[73] Assignee: The United States of America as represented by the Secretary of the Navy, Washington, D.C.

[21] Appl. No.: 910,378

[22] Filed: Jul. 8, 1992

[51] Int. Cl.$^5$ ............................................. G01N 21/76
[52] U.S. Cl. .................................... 356/28; 250/561; 422/52
[58] Field of Search ...................... 356/28; 250/561 C; 422/52

[56] References Cited

U.S. PATENT DOCUMENTS 3,359,973 12/1967 Hoffman.
4,563,331 1/1986 Losee et al. .................. 250/361 CX
4,978,854 12/1990 Lapota et al. .................. 250/361 C

OTHER PUBLICATIONS

J. F. Case, et al; Abstract entitled "Quantitive Measurement of Marine Bioluminescence", Dec. 15, 1987, vol. 68, No. 50, p. 1695.
J. Aiken & J. Kelly; "A Solid State Sensor for Mapping & Profilling Stimulated Bioluminescence in the Marine Environment", vol. 3, No. 4, 1984, pp. 455-464.

Primary Examiner—Mark Hellner
Attorney, Agent, or Firm—Thomas E. McDonald; Alfons F. Kwitnieski; James T. Busch

[57] ABSTRACT

A high intake, defined excitation, vertical profiling survey bioluminescence bathyphotometer system designed to measure, from a statistically significant sample with a calibrated hydromechanical stimulus, (1) the bioluminescence of phytoplankton and zooplankton organisms in the oceanic water column to depths of 400 meters in absolute units of photons per second per volume (intensity) or photons per volume (total flux), (2) the concentration of bioluminescent population in flashes per volume, (3) the average light intensity per bioluminescent event, and (4) population flash dynamics.

19 Claims, 8 Drawing Sheets

BIOLUMINESCENCE BATHYPHOTOMETER

BACKGROUND OF THE INVENTION

1. Technical Field

The invention relates generally to bathyphotometers, and, in particular, to a vertical profiler for measuring stimulated bioluminescence.

2. Background Information

The need for direct measurements of oceanic plankton distribution has lead to the development of optical instrumentation designed to provide data which can be correlated with organism distribution patterns. Such instruments as the beam transmissometer and fluorometer have gained widespread use and with appropriate calibrations allow direct intercomparison of results collected by different investigators. Bathyphotometers designed to measure light from the large number of planktonic organisms which are bioluminescent, have not achieved similar status, although bioluminescence has been promoted as a highly specific bio-optical assay. Lack of comparability in sampling efficiency and differences in bioluminescence excitation and measurement among bathyphotometer designs has been a serious detriment to the general utility of bioluminescence measurements.

There are two types of bathyphotometers: those which measure unstimulated or spontaneous bioluminescence and, more commonly, those designed to measure stimulated bioluminescence. The latter have the greatest potential utility for rapid vertical profiling of the water column and a large number of different designs have been employed for this purpose. One design has been an open field detector which depends on movement of the instrument through the water to stimulate bioluminescence. Stimulation has also been achieved using a disc equipped with "brushes" rotating in open water at a fixed orientation to a detector. Detectors viewing an enclosed volume may depend on movement of the detector through the water to generate turbulence, but usually a pump is used to draw water through the detection chamber and turbulence is generated by an impeller or constriction. For example, a paper by J. Aiken and J. Kelly entitled *A Solid State Sensor for Mapping and Profiling Stimulated Bioluminescence in the Marine Environment*, published in CONTINENTAL SHELF RESEARCH, Vol. 3, No. 4., pp. 455-464, 1984, describes a towed bathyphotometer having a 2.6 cm inlet diameter and a detector dwell time of 25 milliseconds at the maximum flow rate of 1.5 liters per second, with excitation of bioluminescent organisms being produced partly by undefined turbulence and partly by a turbine flowmeter.

In the past, oceanography scientific researchers have utilized small intake pumped bathyphotometers with various types of uncalibrated mechanical stimulation of light. The maximum flow rates of these known bathyphotometers did not exceed 1.5 liters per second, which was not considered statistically significant. Thus, instruments were typically held at various depths for relatively long periods of time, up to 30 minutes, in attempts to quantify the stimulated light. In addition, these sensors were initially designed for near coastal phytoplankton work and almost completely missed the equally prominent offshore zooplankton population. Data from various bathyphotometers have been difficult to correlate to each other and to any standards because of their varied and low pumping rates as well as their various excitation mechanisms and detector dwell times.

SUMMARY OF THE INVENTION

It is an object of the invention to provide a vertical profiling survey bioluminescence bathyphotometer for measuring the bioluminescence of phytoplankton and zooplankton organisms in the oceanic water column in absolute light units from a statistically significant sample with a calibrated hydromechanical stimulus.

It is a further object of the invention to provide this bathyphotometer wherein the measured bioluminescence is essentially the total stimulatable light of the water column sample.

It is a still further object of the invention to provide this bathyphotometer wherein the bioluminescent particle count of the water column sample is measured.

It is another object of the invention to provide this bathyphotometer wherein the bioluminescent temporal decay constant is measured.

It is yet another object of the invention to provide a vertical profiling survey bioluminescence bathyphotometer which samples at a sufficiently high rate to (a) effectively sample all types of bioluminescent sources, including the larger zooplankton now considered to be major contributors to oceanic bioluminescence, and (b) obtain robust statistical evaluations of total stimulable light as a function of depth in durations of time brief enough not to interfere with other ship operations.

The vertical profiling oceanic survey system, according to the invention, includes four interactive subsystems: (1) a bathyphotometer subsystem, (2) a Conductivity, Temperature, Depth, Tilt (CTDT) subsystem, (3) a deployment subsystem, and (4) a shipboard computer subsystem.

The CTDT subsystem is a commercially available unit which supplies the survey system with information on electrical conductivity, temperature, and depth of the surrounding seawater, as well as X and Y axis tilt data.

The deployment subsystem includes a commercially available portable winch spooled with 600 meters of double-armored coaxial cable, a cable sheave suitable for attachment to a ship's A-frame or crane, and a stainless steel cage which incorporates within its structure the CTDT subsystem and the bathyphotometer subsystem.

The bathyphotometer subsystem includes a tubular bathyphotometer, a power supply pressure housing, an electronics pressure housing, and a junction box for interconnecting all of the subsystems and the pressure housings.

The bathyphotometer is essentially a long tube composed of an intake section, a detector chamber, a thruster section, and an exhaust section.

The intake section has a hydrodynamically designed entry cone, a helical light baffle, and a stimulus screen. The detector chamber includes an optical wedge and fiber optic array for bioluminescent particle counting, and white PVC tubing with alternating fiber-optic triplets arrayed longitudinally.

The thruster section includes an expansion cone flanged to the detector section, having within a coaxially mounted ⅛ HP, D.C. motor magnetically coupled to a propeller which supplies the thrust for the high flow rates obtainable with this system.

The exhaust section generally includes a light baffle.

The shipboard computer subsystem includes a Compaq. 386 microcomputer, a printer/plotter for hard copy, a bulk data storage device, power supplies, and an interface unit. All mechanically sensitive units are shock-mounted in two shipping containers, which can be interlocked at sea and used as operating consoles.

After deployment of the cage carrying the bathyphotometer subsystem and the CTDT subsystem, a controlled vertical descent of the cage is maintained, while bioluminescence data, CTDT data, and system status data are acquired by the appropriate sensors, digitized, and transmitted to the topside computer system for analysis, storage and display. The system allows the operator to control various parameters of the subsystems via menu-driven software displayed on a color monitor. System commands, which can be altered at any time by the operator in manual mode, are made by standard keyboard entry. System operating modes and parameters under operator control include thruster speed (and concomitantly, flow rate and volume), photomultiplier sensitivity, photomultiplier gain, real-time data analysis, graphics display mode, vertical deployment rate, and data storage and retrieval. Provisions are also made for standard set-up files to enable the operator to preset parameters. Thereafter, a vertical bioluminescence profile may be run with a single keystroke.

The foregoing and other objects, features and advantages of the present invention will become apparent from the following detailed description of preferred embodiments, taken in conjunction with the drawings which are briefly described below.

DESCRIPTION OF THE PREFERRED EMBODIMENT

The vertical profiling oceanic survey system includes four interactive subsystems: (1) the bathyphotometer subsystem, (2) the CTDT subsystem, (3) the deployment subsystem, and (4) the shipboard computer subsystem.

CTDT Subsystem

The preferred CTDT subsystem is a commercially available unit, namely, the InterOcean S4 CTDT manufactured by InterOcean Systems, San Diego, Calif., which supplies the survey system with information on the electrical conductivity and temperature of the surrounding seawater, as well as the depth and X and Y axis tilt data. The InterOcean S4 CTDT is a self-contained unit equipped with rugged tungsten probes for the CDTD monitoring and an internal flux-gate magnetometer for two dimensional x-y tilt data. All components of the system are housed in a 25 cm glass-reinforced polymer sphere 14, shown in FIGS. 1-4, which is neutrally buoyant in seawater and is deployable to 1000 meters depth.

Deployment Subsystem

The deployment subsystem includes a commercially available portable winch (not shown), such as the 3 HP InterOcean Model 1673-3LW winch equipped with low-noise, electrical slip rings, spooled with 600 meters of 5/16"double-armored coaxial cable 22 (Rochester, type 2-H2), a cable sheave (not shown) suitable for attachment to a ship's A-frame or crane, and a bathyphotometer support frame 26, shown in FIGS. 1-4, which is supported by the cable 22. The frame 26 is constructed of 2.5 cm diameter stainless steel. The top side of the frame 26 includes four lifting lugs 28 which are utilized with other structural support members (not shown in the drawings) to connect the frame 26 to the cable 22. The frame 26 also incorporates within its structure the spherical housing 14 for the CTDT subsystem, as shown in FIGS. 1-4.

Bathyphotometer Subsystem

The bathyphotometer subsystem is a vertical profiling survey bioluminescence bathyphotometer system designed to measure, from a statistically significant sample with a calibrated hydromechanical stimulus, (1) the bioluminescence of phytoplankton and zooplankton organisms in the oceanic water column to depths of 400 meters in absolute units of photons per second per volume (intensity) or photons per volume (total flux), (2) the concentration of bioluminescent population in flashes per volume, (3) the average light intensity per bioluminescent event, and (4) population flash dynamics.

Referring to FIGS. 1-4, the bathyphotometer subsystem includes a high intake, defined excitation (HIDEX) bathyphotometer 30, a power supply pressure housing 32, an electronics pressure housing 34, and a junction box 36, as shown in FIGS. 1-4. The junction box 36 is used for electrically interconnecting the HIDEX bathyphotometer 30 and the pressure housings 14, 32.

The HIDEX bathyphotometer 30 is essentially a long tube having a horizontal axis A—A and defining an axial passage 38 through which seawater is drawn, as shown in FIGS. 1-4. In the past, bathyphotometers have had a vertically extending axial passage. However, the HIDEX bathyphotometer 30 has a horizontally extending axial passage 38 in order to minimize the effect of swells or other conditions causing vertical movement of the ship on the flow rate of seawater through the passage 38. The HIDEX bathyphotometer 30 includes an intake section 40, a detector chamber 42, a thrustor section 44, and an exhaust section 46.

Figure 1:
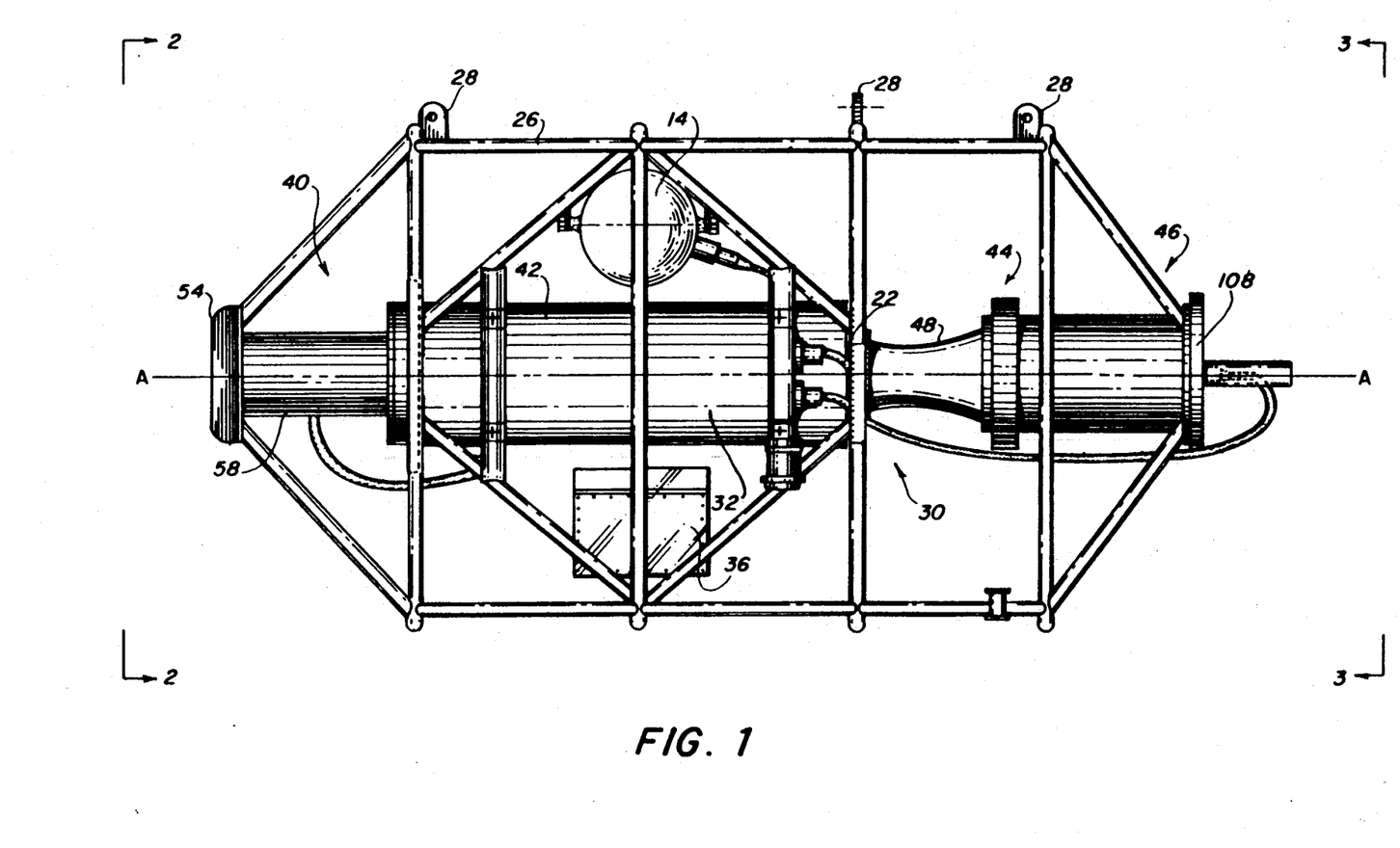
FIG. 1 is a side view of the submersible portion of the vertical profiling oceanic survey system, according to the invention.
Figure 2:
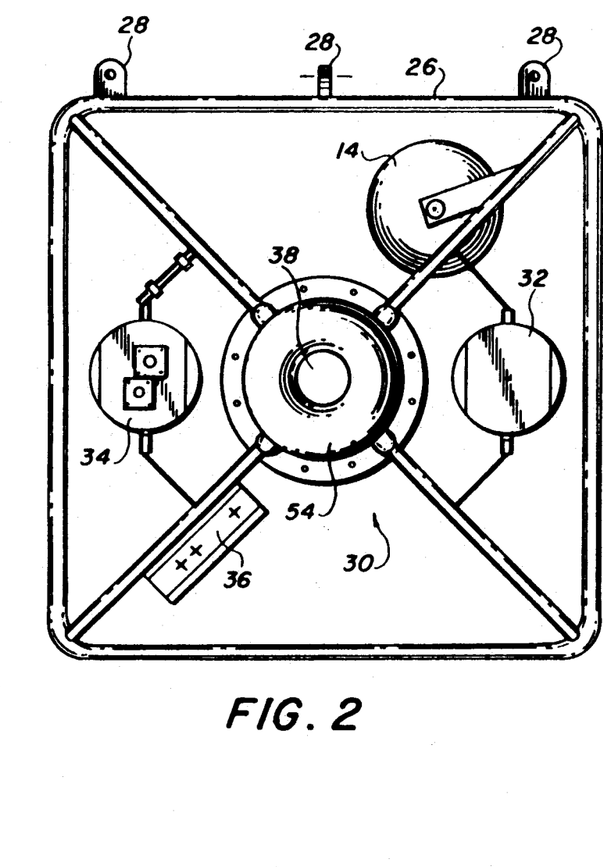
FIG. 2 is an end view of the submersible portion of the vertical profiling oceanic survey system of FIG. 1, taken along the line 2—2 of FIG. 1.
Figure 3:
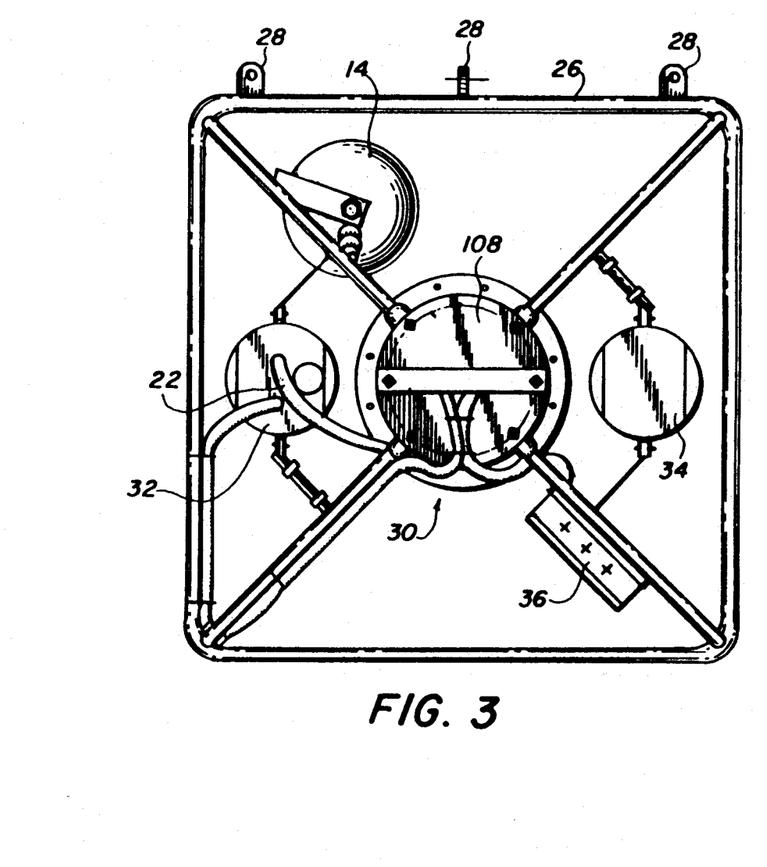
FIG. 3 is an end view of the submersible portion of the vertical profiling oceanic survey system of FIG. 1, taken along the line 3—3 of FIG. 1.
Figure 4:
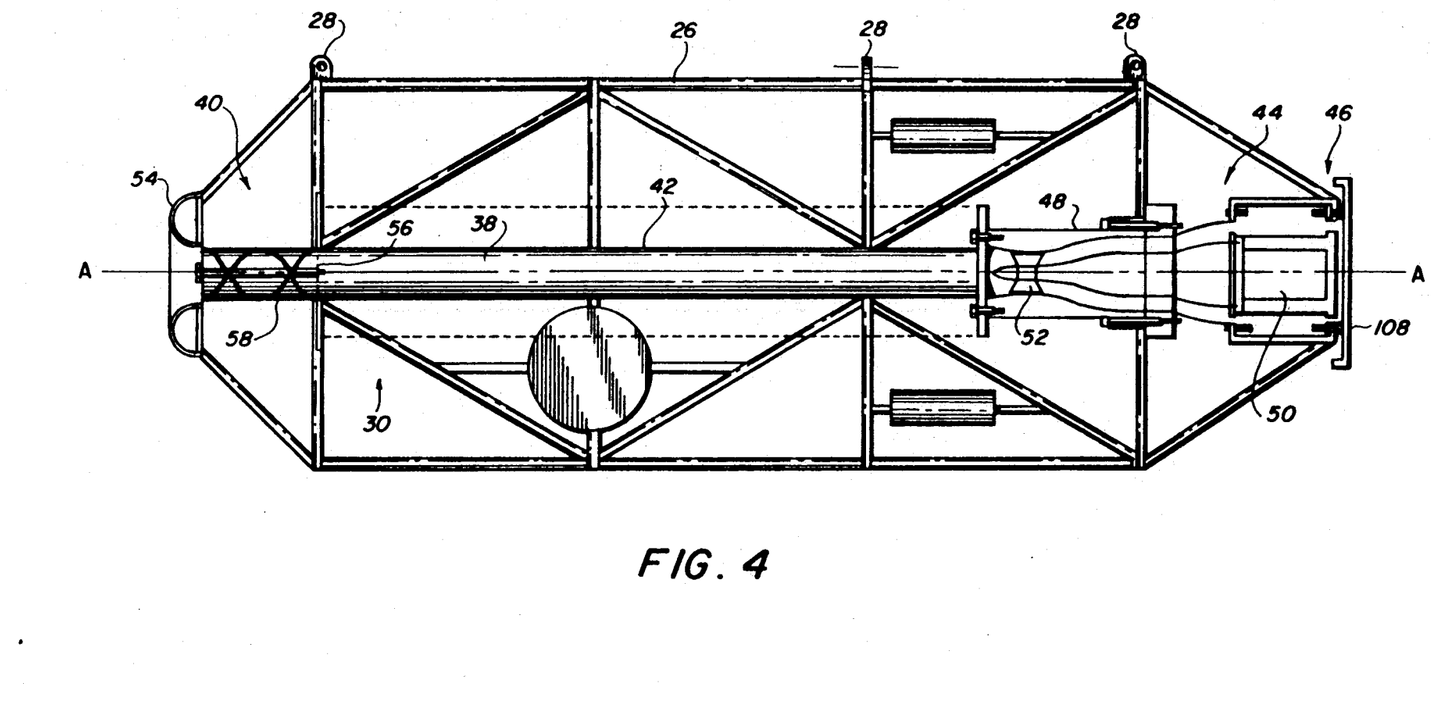
FIG. 4 is a side view of the submersible portion of the vertical profiling oceanic survey system, with outer portions of the bathyphotometer removed to show interior elements.
Figures 8, 9:
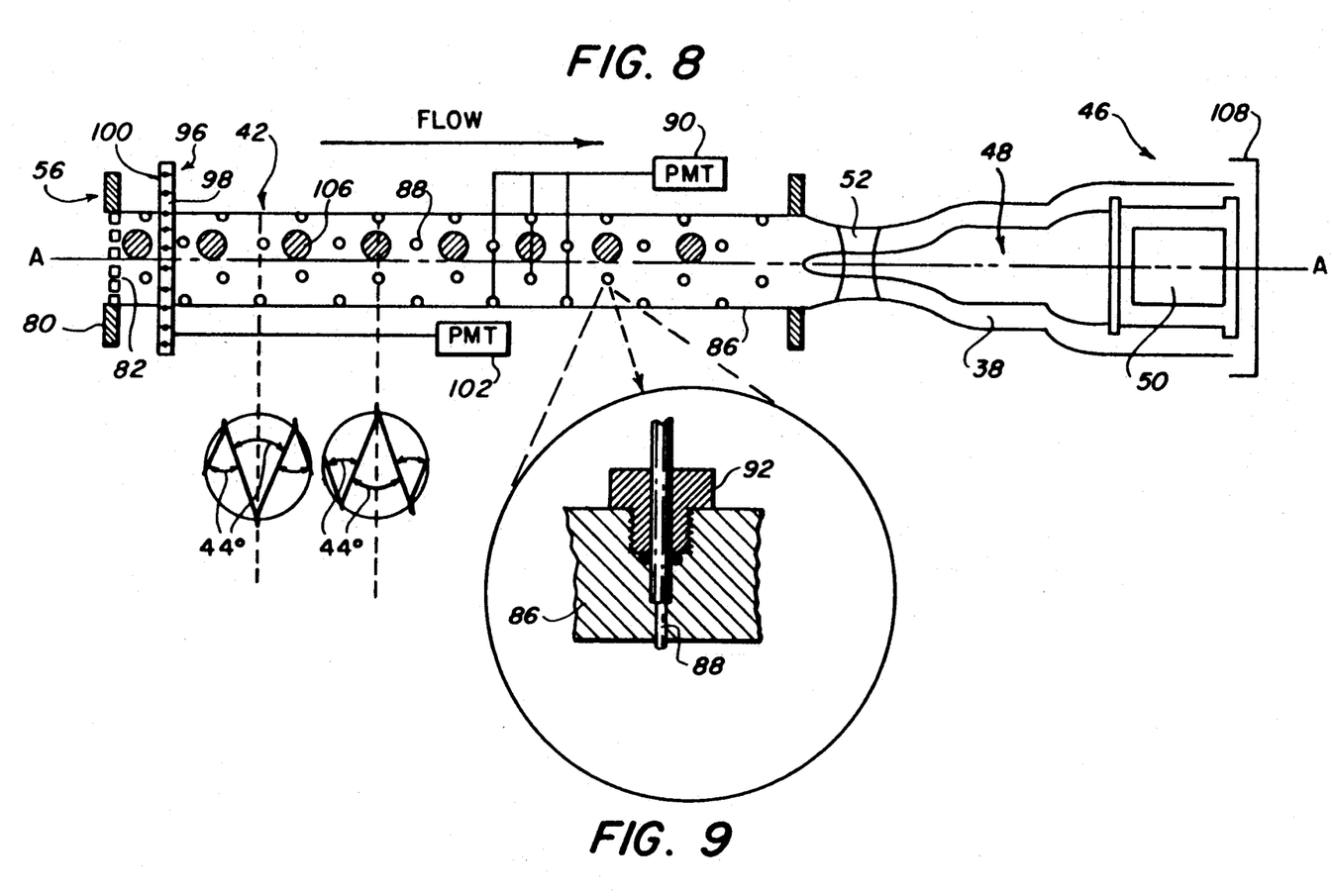
FIG. 8 is a schematic side view of the detector chamber, thruster section, and exhaust section of the bathyphotometer.
FIG. 9 is an enlarged cross-sectional view of a single optical fiber holder, which is mounted in the detector chamber wall of FIG. 8.

The thrustor section 44 includes a ⅛ horsepower permanent magnet DC pump 48, manufactured by Inertial Motors Corporation, which draws seawater through the axial passage 38 extending through all of the HIDEX bathyphotometer sections 40, 42, 44, and 46. The pump 48 includes a variable speed d.c. motor 50 magnetically coupled to a propeller 52 within the axial passage 38, as shown in FIGS. 4 and 8.

The portion of the axial passage 38 extending from the intake section 40 through the detector chamber 42 has a uniform diameter of approximately 12.7 cm., which exceeds the inlet diameter of previous bathyphotometers by at least one order of magnitude and permits high pumping rates.

The intake section 40 includes an entry cone 54, affixed to the frame 26, a excitation grid assembly 56 also affixed to the frame 26, and a helical light baffle assembly 58 disposed between the entry cone 54 and the excitation grid assembly 56.

Since premature excitation had been a problem with some bioluminescence detectors, the entry cone 54 is hydrodynamically designed to maintain an initial laminar flow and to effect the transition from zero to maximum flow with minimum turbulence at the inlet to the axial passage 38.

A early embodiment or predecessor of the helical light baffle assembly 58 included an axially-extending cylindrical support member which defined a portion of the axial passage 38 and which had affixed therein a helical light baffle having a relatively long pitch of approximately 30.5 cm. to minimize turbulence in seawater flowing therethrough. This predecessor helical light baffle assembly was rotatably connected to the entry cone 54 and the excitation grid assembly 56 by respective ball thrust bearings so as to be freely rotated about the bathyphotometer axis A—A by the flow of seawater through the axial passage 38. Both the cylindrical support member and the helical light baffle affixed therein were formed of aluminum having a hard anodized black finish to minimize light reflection.

Although this predecessor light baffle assembly was advantageous in that it would respond equally as well to the flow of seawater through it in either direction, the use of this early helical light baffle assembly produced a reduction in the measured bioluminescence of approximately five per cent of that measured without the light baffle assembly, indicating some premature excitation of the bioluminescent organisms in the water flowing through the light baffle assembly. To reduce such premature excitation, the present helical light baffle assembly 58 was designed and tested. While there may still be some premature excitation of the bioluminescent organisms in the seawater flowing through the present light baffle assembly 58, it is difficult to detect any reduction in the measured bioluminescence when the light baffle assembly 58 is used over that measured when no light baffle was used. Certainly, any such reduction in measured bioluminescence caused by the light baffle assembly 58 is much less than five per cent.

Figure 5:
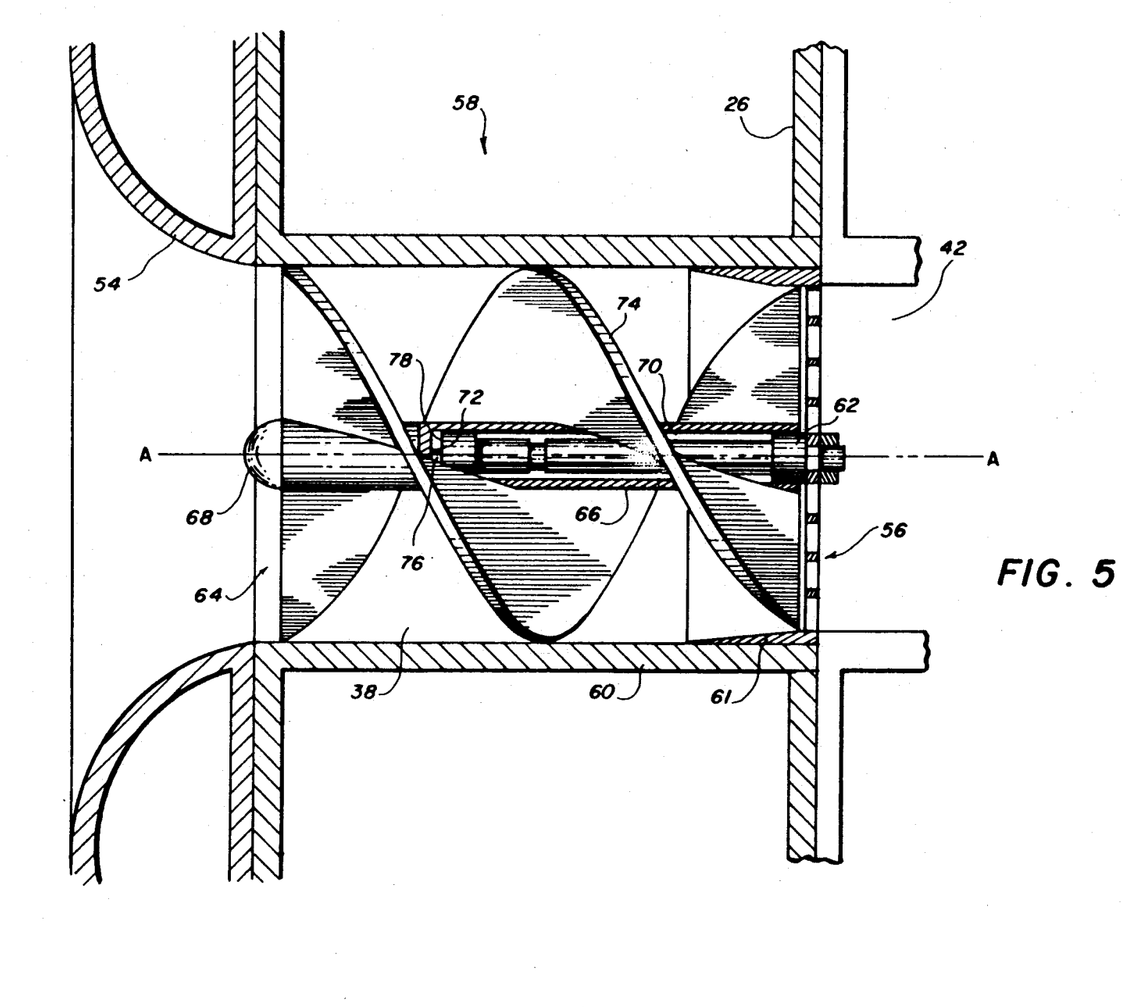
FIG. 5 is a side view of the bathyphotometer helical light baffle assembly, with some outer portions removed to show interior elements.

The preferred helical light baffle assembly 58 shown in FIG. 5 includes: (1) an open-ended cylindrical side wall 60 which is affixed to the frame 26 to form the portion of the axial passage 38 between the entry cone 54 and the excitation grid assembly 56, the inner diameter of the side wall 60 being gradually reduced to about 12.7 cm. adjacent the grid assembly 56 by a tapered cylindrical insert 61; (2) an axially-extending support spindle 62 affixed to the excitation grid assembly 56; and (3) a rotor 64 of lightweight non-reflecting material, e. g., black-colored molded plastic material, such as Delgrin, manufactured by DuPont. The rotor 64 has a cylindrical center portion 66 having a rounded or streamlined front hub 68 to minimize turbulence in the seawater flowing around it. The rear end of the rotor center portion 66 includes an axial center bore 70 into which the free end 72 of the support spindle 62 projects. The rotor 64 also includes a helical flight portion 74 which extends for one turn (30.5 cm pitch distance) about the center portion 66. The outer diameter of the helical flight portion 74 is tapered inward along the end quarter turn of the flight portion adjacent the grid assembly 56 to conform to the taper of the side wall insert 61, to thus prevent external light from entering the detector chamber 42 through the annular clearance space between the rotor 64 and the side wall 60. The free end 72 of the support spindle 62 carries a single ball bearing 76 which is held in contact with a radially-extending flat surface 78 of the rotor center portion 66 at the closed end of the axial bore 70 whenever seawater is drawn through the light baffle assembly by the thrustor pump. This single ball bearing 76 permits the rotor 64 to be freely rotated about the axis A—A by the seawater flowing through the light baffle assembly 58.

Figure 6:
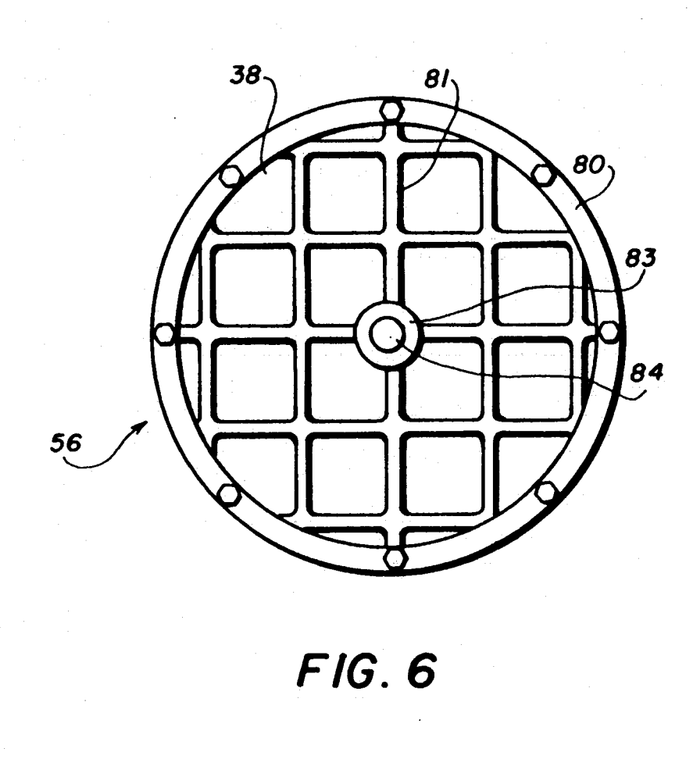
FIG. 6 is a front view of a first embodiment of the bathyphotometer excitation grid assembly.
Figure 7:
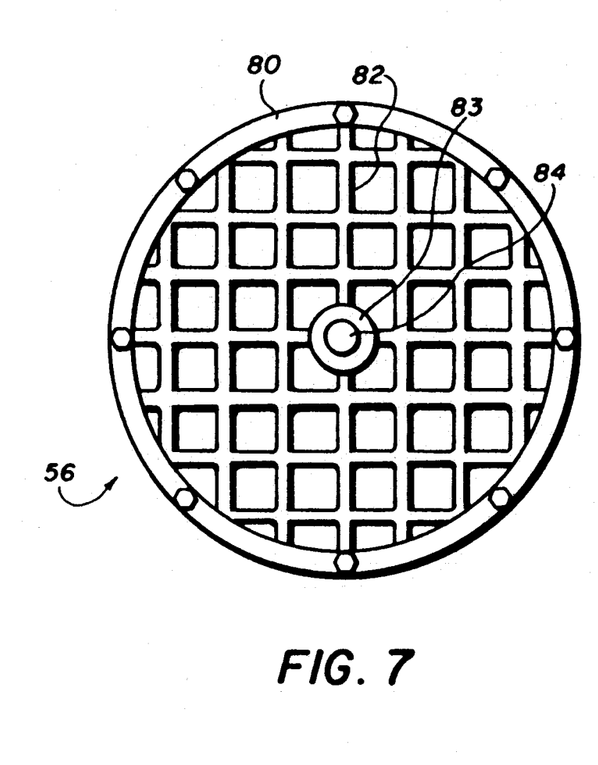
FIG. 7 is a front view of a second embodiment of the bathyphotometer excitation grid assembly.

There are four standard embodiments of the excitation grid assembly 56 which have been calibrated and tested, two of which are shown in FIGS. 6 and 7. These excitation grid screen assemblies 56 include a flange 80 having a center opening which defines a portion of the axial passage 38. In the embodiment of FIG. 6, an excitation grid 81 (2.5 cm.×2.5 cm. grid size, 20% solidity) is affixed to the flange 80 within the axial passage 38 to introduce turbulence in the seawater flowing therethrough. In the embodiment of FIG. 7, a different excitation grid 82 (1.5 cm.×1.5 cm. grid size, 30% solidity) is used for the same purpose. Both the grid 81 of FIG. 6 and the grid 82 of FIG. 7 have a circular center portion 83 (⅞" dia.) defining an axial bore 84 (⅜" dia.) for securing the support spindle 62 of the light baffle assembly 58. The flange 80 and center portion 83 have a uniform thickness of approximately a quarter inch. One of the two embodiments of the excitation grid screen assembly 56 which are not shown in the drawings includes an excitation grid having a 2.5 cm.×2.5 cm. grid size and 30% solidity, and the other unshown embodiment includes an excitation grid having a 1.5 cm.×1.5 cm. grid size and 20% solidity.

Figure 10:
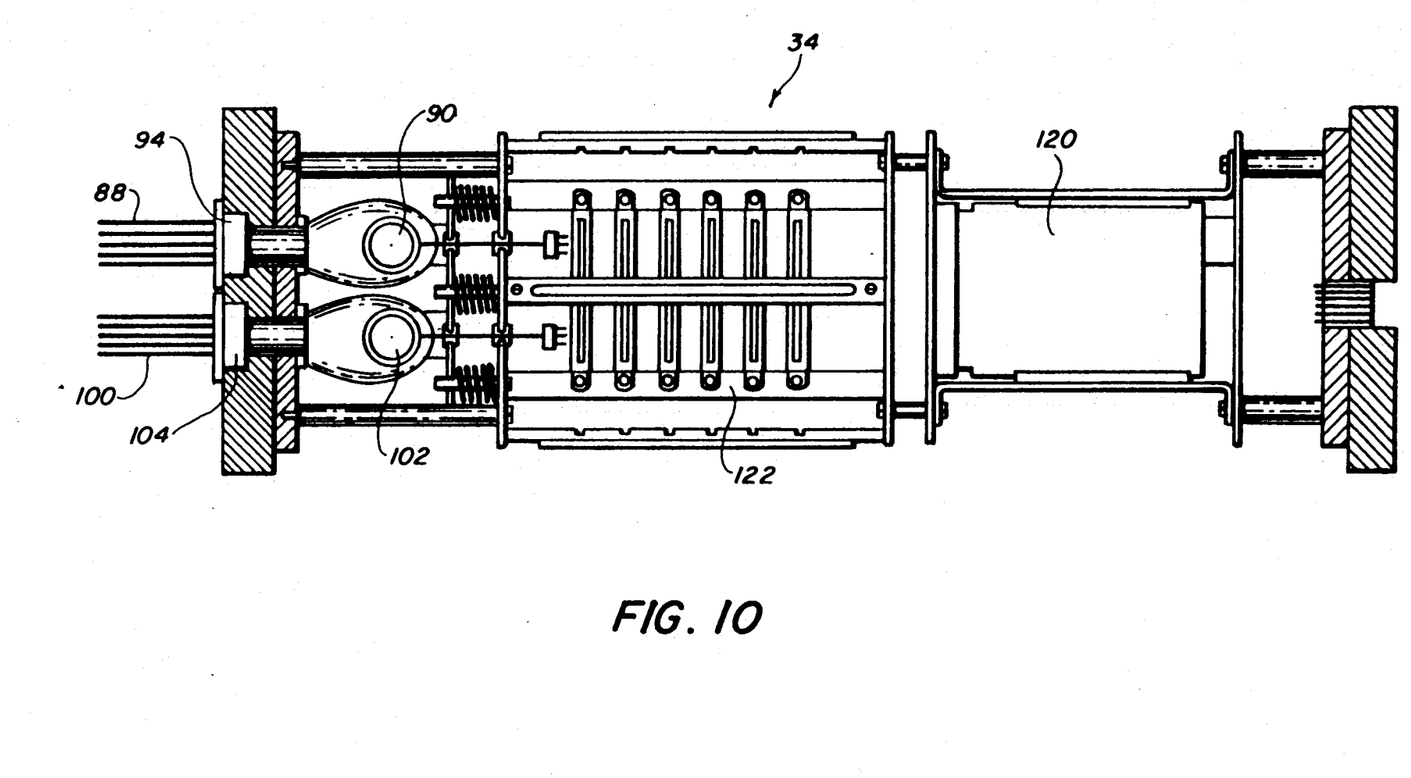
FIG. 10 shows the electronics pressure housing assembly, with the side wall removed.
Figure 11:
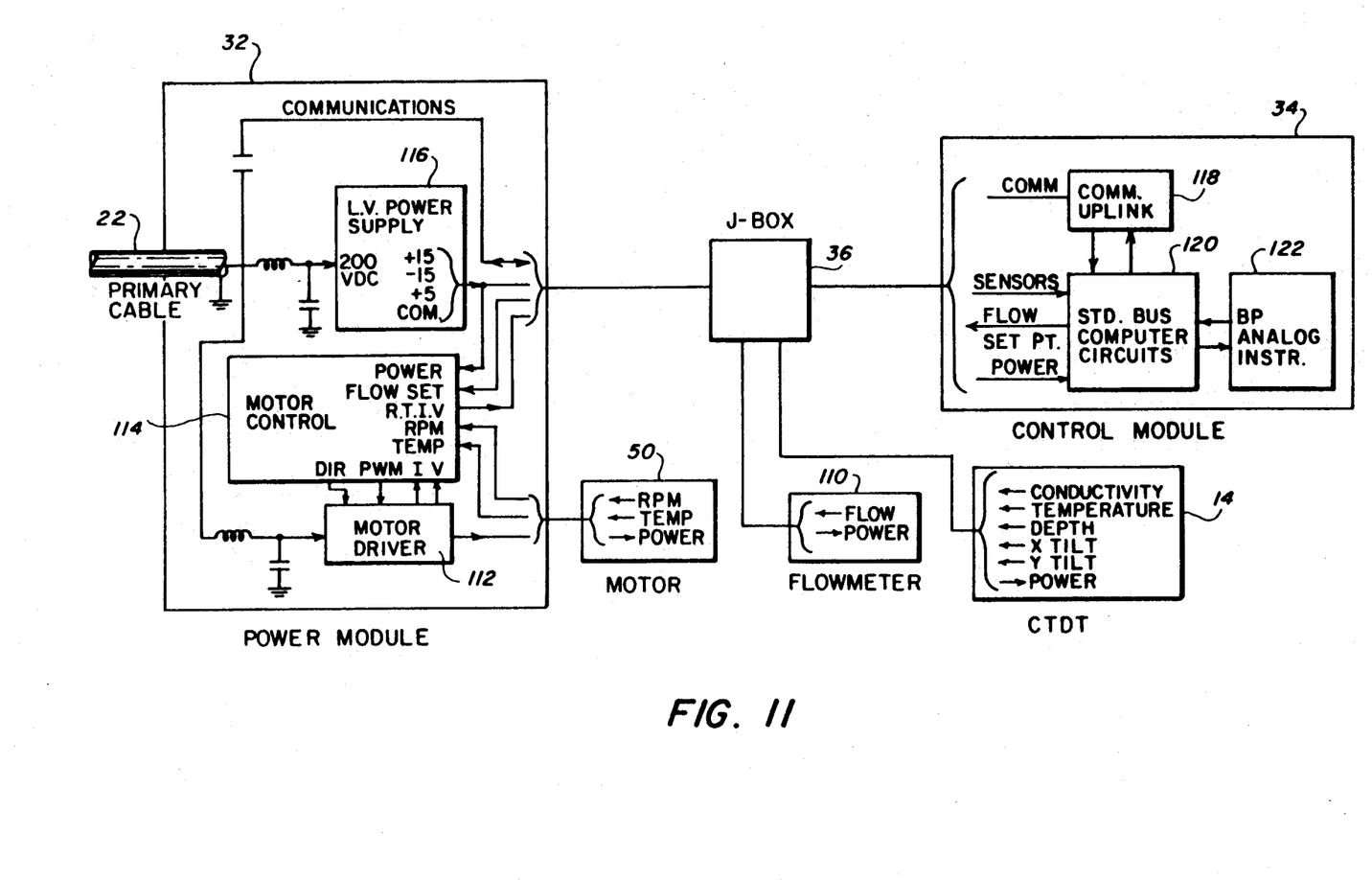
FIG. 11 is an electrical schematic block diagram of the submersible portion of the vertical profiling oceanic survey system.

Referring to FIG. 8, the detector chamber 42, defined by a white cylindrical PVC tube 86, is a light integrating cylinder designed to maximize light gathering efficiency while reducing bias due to an organism's orientation with reference to the detector, a critical consideration with zooplankton since their light emission is frequently highly directional. The length of the detection chamber 42 (1.3 m.) was designed to produce a residence time sufficiently long enough to measure the total light output from a single dinoflagellate flash at the maximum pumping rate. The measuring volume of the detection chamber 42 is 16 liters. Integrated light detection is by means of fifty-seven fiber optics 88 (AMP, 1 mm. multimode plastic) leading to a first side window photomultiplier tube 90 (RCA 931B) in the electronics pressure housing. The optical fibers 88, which have a 44° acceptance angle in seawater, are arranged in a minimally overlapping array of alternating fiber-optic triplets along the length of the PVC tube 86, providing 90° coverage of the detection chamber 42. As shown in FIG. 9, polished ends of the optical fibers 88 are held with respective quick-change PVC holders 92, in the detection chamber wall 86, so that each fiber 88 can be individually replaced. The fibers 88 are gathered and bundled in a Sylastic J-RTV mold positioned against a 12 mm thick polycarbonate window 94 viewed by the first photomultiplier tube 90 in the electronics pressure housing 34, as shown in FIG. 10.

Referring again to FIG. 8, an optical wedge narrow field detector assembly 96, including an annular optical fiber holder 98 and sixteen optical fibers 100 leading to a second photomultiplier tube 102 in the electronics pressure housing 34, is disposed peripherally around the PVC tube 86 about an inch along the axis A—A from the excitation grid 82. The ends of the optical fibers 100, which are equally spaced about the axis A—A, detect bioluminescence in the detector chamber 42 through silvered slots in the holder 98 and PVC tube 86 which permit only a 7° longitudinal field of view but a 54° lateral field of view. The optical fibers 100 are gathered and bundled in a Sylastic J-RTV mold positioned against a second 12 mm. thick polycarbonate window 104 viewed by the second photomultiplier tube 102 in the electronics pressure housing 34. Thus, the optical wedge narrow field detector 96 views only a narrow cross section of the entrained water flowing through the detector chamber 42, and is used in conjunction with the second photomultiplier tube 102 to count bioluminescent events. Gain and sensitivity of both photomultiplier tubes 90, 102 are remotely controllable from the surface.

The detector chamber 42 also includes an array of eight photodiodes 106 which are evenly distributed down the length of the chamber and are flush mounted in the chamber wall 86. Each photodiode 106 generates a signal proportional to the light emitted by bioluminescent organisms in the seawater flowing through the detector chamber 42 while these bioluminescent organisms are within the field of view of the photodiode. The output data from this array of photodiodes 106 is utilized by the surface computer and control system for realtime calculation of population flash dynamics. Also, the output data from the last photodiode 106 can be utilized to adjust the flow of seawater through the detector chamber 42 to prevent light ejection, i. e., to make certain the transit time of the seawater through the detector chamber 42 is sufficiently long that the light-generating ability of all bioluminescent organisms stimulated by the turbulence generating grid 82 is exhausted while these bioluminescent organisms are still in the detector chamber 42.

The detector chamber 42 must be sufficiently shielded from external light at both ends to permit daylight operations in shallow water. To prevent light from entering from the exhaust end of the chamber, the propeller 52 and the portion of the passageway 38 extending from the rear end of the detector chamber 42 to the exhaust section 46 has a dull black finish. In addition, the exhaust section 46 may include a back baffle plate 108 having a dull black finish to further shield the detector chamber 42 from external light.

The HIDEX bathyphotometer also includes a flowmeter 110 (see FIG. 10) for measuring the flow rate of seawater through the bathyphotometer and generating an electrical signal proportional to this flow rate. In FIG. 5, for example, the rotor 64 of the helical light baffle assembly 58 can include an insert of magnetic material at its outer periphery which actuates an electromagnetic revolution counter affixed to the cylindrical side wall 60 adjacent to the path of the rotating magnetic insert. Alternatively, magnetic material could be incorporated into the plastic material from which the rotor 64 is formed. Capacitance or conductance sensing devices could also be used with the helical light baffle assembly 58 as the flowmeter 110. The electrical characteristics of the rotor 64 could be optimized by adding conductive or insulating material to the material from which the rotor 64 is formed to enhance the operation of a capacitance or conductance sensing device used as the flowmeter 110.

The power supply pressure housing 32, as shown in FIG. 10, contains a motor driver 112 for the pump motor 50, a motor controller 114 for controlling the speed of the pump motor 50 via the motor driver 112 in accordance with control signals from the surface, and a low voltage power supply 116 for converting a high d.c. voltage (200 v.d.c. supplied from the surface through the coaxial cable 22) to various low d.c. voltages (+5 v., +15 v., −15 v.) required by the motor controller 114, the flowmeter 110, the CTDT subsystem , and the electronic equipment in the electronics pressure housing 34.

The electronics pressure housing 34 includes a data communications uplink 118, a computer board 120, and the bathyphotometer analog instrumentation 122. The analog instrumentation 122 includes the photomultiplier tubes 90, 102 for stimulated light measurements and photoevent counting, and related circuits to amplify and condition photomultiplier tube signals as well as photomultiplier tube anode voltage supplies and monitoring systems for bathyphotometer operational status and leak detection. Analog data signals from the CTDT subsystem are transferred to the electronics pressure housing 34 for digitizing and incorporation into the outgoing data stream to the shipboard computer system.

The shipboard computer subsystem includes a surface computer (Compaq. 386 microcomputer), a printer/-plotter for hard copy, a bulk data storage device, power supplies, and an interface unit. All mechanically sensitive units are shock-mounted in two shipping containers, which can be interlocked at sea and used as operating consoles.

The surface computer controls the data acquisition sequence via the coaxial cable 22 from the surface subsystem which terminates in the power supply pressure housing 32. The surface computer sends acquisition commands to the HIDEX bathyphotometer 30, activates the pump motor 50, controls the pump motor speed and direction of rotation, sets photomultiplier tube voltage and gain and stores and displays the acquired photometric and environmental data, as well as data regarding the operational status of the bathyphotometer.

The HIDEX bathyphotometer has two modes of operation. The system initializes in the standby mode. In this standby mode, the system acquires status information once per second, including CTDT data, motor voltage, current and RPM, and primary cable voltage, and sends it to the surface computer. On command from the surface computer, the HIDEX bathyphotometer enters the profiling mode. In the profiling mode, the voltage signal from the first multiplier tube 90 is sampled at 500 Hz. A thousand bytes of photomultiplier data are sent with 24 bytes of status data as a 1024 byte block at a rate of two blocks per second.

The system is capable of rapid data reduction and analysis. The onboard computer system displays bioluminescent data and system status in real time during vertical casts. Environmental data, including conductivity, temperature, depth and tilt are recorded during casts and are available for display on demand. Bioluminescence data in absolute photons can be plotted as a function of depth, in conjunction with temperature and salinity or as a function of either of these parameters. Data sampling rate (256 kilobaud/sec) allows expansion of areas of interest to reveal small scale detail.

After deployment of the cage 26 carrying the bathyphotometer subsystem and the CTDT subsystem, a controlled vertical descent of the cage 26 is maintained, while bioluminescence data, CTDT and tilt data, and system status data are acquired by the appropriate sensors, digitized, and transmitted to the topside computer system for analysis, storage and display. The system allows the operator to control various parameters of the subsystems via menu-driven software displayed on a color monitor. System commands, which can be altered at any time by the operator in manual mode, are made by standard keyboard entry. System operating modes and parameters under operator control include thruster speed (and concomitantly, flow rate and volume), photomultiplier sensitivity, photomultiplier gain, real-time data analysis, graphics display mode, vertical deployment rate, and data storage and retrieval. Provisions are also made for standard set-up files to enable the operator to preset parameters. Thereafter, a vertical bioluminescence profile may be run with a single keystroke.

Hydrodynamics

During operation of the HIDEX bathyphotometer 30, laminar flow is maintained through the device until the onset of turbulence at the excitation grid 82. Turbulence is generated with a defined geometry and for a defined distance downstream of the excitation grid 82. Sheer forces within the turbulent field stimulate bioluminescence emission from organisms resident within the water column. Maximal stress is exerted at the screen 82 and little additional stress is imposed through the remainder of the detection chamber 42. Consequently, excitation is well defined, as compared with other bathyphotometers, making it possible to obtain flash kinetics from individual organisms passing through the system.

A pumping rate of 680 liters/min. produces an effective capture volume immediately ahead of the entry cone 54 of 4500 cc. for organisms with escape velocities less than or equal to 10 cm./sec. This is a greater than 500% improvement over pre-existing bathyphotometers permitting high capture efficiency without species bias since the maximal escape speed reported for most organisms of interest is about 25 cm./sec. and most are at 10 cm./sec. or less.

Radiometric Calibration

In order to determine the relationship between absolute photon flux in the detector chamber 42 and photomultiplier tube output a $^{14}C$-phosphor standard was constructed. The standard was prepared using a procedure provided by W. H. Biggley (Johns Hopkins University), using $^{14}C$ as the exciter and a recently developed high quantum efficiency, television cathode-ray-tube phosphor, Sylvania Type 1330, as the emitter. The standard was formed as a solid epoxy cast in a pyrex tube (4 mm. I.D. 6 mm. O.D.) approximately 913 mm. long. Four other tubes of the same diameter were also cast from the same batch of $^{14}C$-phosphor and epoxy in lengths of 15, 33, 53, and 73 mm. These tubes were small enough to measure in an integrating sphere-photon counting system (Latz et al., 1987). Photon flux of each tube was measured to determine the average photon flux per mm of $^{14}C$-phosphor rod and this value was used to calculate the photon flux for the 913 mm. long transfer standard. The power spectral density of the standard is a close match to that of midwater bioluminescence. The peak emission for the standard is at 450 nm. with a full-width at half maximum of 55 nm. and the photon flux is $1.5 \times 10^{10}$ photons per second. Due to the long half-life of $^{14}C$ the intensity loss will be less than 0.01% per year. For calibration of the HIDEX bathyphotometer the $^{14}C$-phosphor rod is suspended on the axis A—A in the detector chamber 42 and a transfer function is applied in software between known photon flux and PMT output so that computer readout is displayed in absolute photons per second.

Biological Calibration

Laboratory cultures of bioluminescent dinoflagellates were used to biologically calibrate a test HIDEX bathyphotometer, which is similar to the HIDEX bathyphotometer described herein except it has a full scale, transparent, plexiglass detector chamber, but does not have a helical light baffle assembly. Cultures of *Pyrocystis noctiluca* (Murray), *Pyrocystis fusiformis* (Murray) and *Gonyaulax polyedra* (Stein) were grown in unialgal culture at 20±2° C. in filtered seawater, enriched with "F/2" formula (Guillard and Ryther, 1962) minus silicate and plus soil extract (1%). Culture densities were measured with a Sedgewick hemocytometer. All biological calibration experiments were conducted in a darkened seawater test tank with the test HIDEX bathyphotometer mounted horizontally. The dinoflagellates, maintained on a 12-hour light (1mW cm$^{-2}$), 12-hour dark cycle, were loaded into delivery systems in day phase when cells do not flash in response to mechanical stimulation. Care was taken to minimize mechanical stimulation of cells prior to each experiment since stimulus history can radically affect the intensity and kinetics of the bioluminescent flash.

The spatial distribution of stimulated bioluminescence in the detector chamber was recorded using an ISIT (intensified silicon intensified target) video camera (Dage 66) viewing the full scale Plexiglas detector chamber. Dinoflagellates released in the sea water test tank directly in front of the test HIDEX bathyphotometer inlet were stimulated to luminesce as they were pulled past the excitation grid into the transparent detector chamber. Computer image analysis of these video recordings was carried out with a Megavision 1042XM image analysis system. The spatial distribution of stimulated bioluminescence in the transparent detector chamber was a function of flash duration and pump speed. Since the delay between stimulus and flash onset for *Pyrocystis fusiformis* is between 15 to 20 ms., the monotonic intensity distribution in the chamber was indicative of a single flash response from most cells with excitation at or near the grid and little reexcitation occurring downstream of the grid.

In order to relate the test HIDEX bathyphotometer measurements of stimulated bioluminescence to the total bioluminescence potential of the dinoflagellates, light measured from 5 ml. aliquots of cells injected into the test HIDEX bathyphotometer was compared to total stimulable light (TSL) from identical aliquots measured in the integrating-sphere, photon-counting apparatus. One hour prior to the onset of night phase, 5 cc. disposable syringes were loaded with a well-mixed culture and were then held in the environmental chambers where the cultures were maintained, until 3 hours after the onset of night phase. Injection of cells into the test HIDEX bathyphotometer was done with the syringe held on the bathyphotometer axis with the detector chamber approximately 25 cm. in front of the entry cone. At this distance, cells ejected at approximately 5 ml. $min^{-1}$ were entrained in the bathyphotometer flow stream without stimulation prior to entering the detector chamber. A plankton net attached to the test HIDEX bathyphotometer exhaust prevented recycling of stimulated cells through the detector chamber. For each 5 cc. aliquot of cells measured in the test HIDEX bathyphotometer, TSL of an equivalent aliquot was determined in the integrating sphere. For TSL measurements, the cells were slowly ejected into a 50 cc. beaker containing 10 cc of seawater. The beaker was held by a clamp in the center of the integrating sphere and cells were stimulated by stirring with a DC motor-driven stirring rod at 2000 rpm. Cells were stirred and counts were accumulated for 80 seconds, a period of time sufficient to exhaust their bioluminescence capacity.

For measurements in both the test HIDEX bathyphotometer and the integrating sphere, care was taken to equilibrate the temperature of the cells with that of the seawater into which they were ejected since temperature differentials of more than 2° C. stimulated bioluminescence.

The percentage of TSL measured in the test HIDEX bathyphotometer was quite different for *Gonyaulax polyedra* than for *Pyrocystis noctiluca*. For *G. polyedra*, test HIDEX bathyphotometer measurements were $94 \pm 19°$ (mean $\pm$ S.D. N=5) of TSL, whereas for *P. noctiluca* they were $12 \pm 3\%$ (mean $\pm$ S.D. N=5). Analysis of single cell responses for both cell types indicated that while *G. polyedra* responded to prolonged stimulation in the integrating sphere with only one flash, *P. noctiuca* responded with 10 or more flashes. These measurements provided further evidence that the test HIDEX bathyphotometer was eliciting a single-flash response without prestimulation.

Excitation for these experiments was provided with a grid having bars 0.31 cm. wide and 0.64 cm. thick, a distance between centers of 1.55 cm., and a solidity of 32%.

Motor speed tests with *P. noctiluca* indicated that at the lowest flow rate tested, 4 liters per second, some portion of the population was stimulated and at a volumetric flow rate of 22 liters per second, the stimulus strength was suprathreshold for the population. Cells were not restimulated as they passed through the turbulent flow downstream of the grid even though increased bioluminescence recorded with introduction of a second grid 50 cm. downstream clearly indicated that re-excitation was possible. Therefore, while the stimulus strength at the grid, at a flow rate of 22 liters per second, was suprathreshold for the population, that 50 cm. downstream of the grid at the same flow rate, was subthreshold.

The design and calibration of the HIDEX bathyphotometer was driven by a desire to create a BP system that could rapidly and reliably profile the water column in conjunction with existing instrumentation for measuring conductivity, temperature, depth, fluorescence and transmission. Given the very large number of planktonic organisms which are bioluminescent, well defined and calibrated measurements of stimulated bioluminescence can provide valuable information about how organisms are distributing themselves relative to the physical and chemical features of their environment.

There are many additions, changes and modifications which can be made to the preferred embodiments of the invention described herein without departing from the spirit and scope of the invention. Therefore, it is to be understood that the invention is not limited to the specific embodiments thereof except as defined in the appended claims.

What is claimed and desired to be secured by Letters Patent of the United States is:

1. A vertical profiling oceanic survey system, including a bioluminescence bathyphotometer which comprises:
   a longitudinal axis;
   a tubular detector chamber, extending along the axis, having an inlet at one end, an outlet at an opposite end, and a capacity of at least 11 liters;
   pumping means, disposed adjacent the detector chamber outlet, for drawing seawater through the detector chamber at a selected rate of flow, the pumping means having a maximum rate of flow of at least 30 liters per second;
   flowmeter means for measuring the flow rate of seawater through the bathyphotometer;
   a calibrated hydromechanical stimulus means, disposed adjacent the detector chamber inlet, for generating a defined turbulence field at the detector chamber inlet to stimulate bioluminescent plankton in the seawater flowing therethrough to generate light; and
   light sensing means for sensing light emitted by bioluminescent plankton in the seawater flowing through the detector chamber.

2. A system, as described in claim 1, wherein the light sensing means comprises total light measuring means for measuring the total light produced by bioluminescent plankton in the seawater flowing through the detector chamber during the residence time of the plankton within the detector chamber, the total light measuring means comprising:
   a light measuring device for generating a signal proportional to the intensity of light received by the light measuring device; and
   a plurality of optical fibers having opposite first and second end, the first ends extending int the detector chamber to receive light generated therein, the first ends being regularly space around the inner perimeter and along the length of the detector chamber to provide optimal coverage of the detector chamber with minimal overlap, the second ends of the optical fibers being bunched to deliver light from the detector chamber to the light measuring device whereby the signal generated by the light measuring device corresponds to the total light generated in the detector chamber.

3. A system, as described in claim 2, wherein the detector chamber has a light-reflecting inner surface to maximize light gathering efficiency while reducing bias due to a bioluminescent organism's orientation within the detector chamber.

4. A system, as described in claim 3, which further comprises a radiometric calibration means for calibrating the total light measuring means to measure the total light generated by stimulated bioluminescent plankton within the detector chamber in absolute light units per time unit, such as photons per second.

5. A system, as described in claim 1, wherein said light measuring means comprises light flash counting means for counting the light flashes within the detector chamber produced by bioluminescent plankton excited by said stimulus means, the light flash counting means comprising:
- a light measuring device for generating a signal proportional to the intensity of light received by the light measuring device; and
- an optical wedge narrow field detector, which includes
  - a plurality of optical fibers having respective first ends and opposite second ends, the second ends being bunched to deliver light received by the optical fiber first ends to the light measuring device, and
  - an annular optical fiber holder means, disposed adjacent the calibrated hydromechanical stimulus means at the inlet end of the detector chamber, for holding the first ends of said plurality of optical fibers so that the first ends are disposed uniformly about the detector chamber in the same radial plane, the fiber holder and the detector chamber having silvered slots through which light from the detector chamber is supplied to the first ends of the optical fibers, the slots being shaped so as to permit a wide lateral field of view but a restricted longitudinal field of view for the first ends of the optical fibers, so that the optical wedge narrow field detector only views a narrow cross section of the entrained water flowing through the detector chamber;

whereby the signal generated by the light measuring device corresponds to the number of bioluminescent events occurring in the detector chamber caused by the calibrated hydromechanical stimulus means.

6. A system, as described in claim 1, wherein said light sensing means comprises:
- a plurality of light measuring devices which are evenly distributed along the length of the detector chamber and are flushmounted in the detector chamber wall, each light measuring device generating a signal proportional to the light emitted by bioluminescent organisms in the seawater flowing through the detector chamber while the bioluminescent organisms are within the field of vision of the light measuring device; and
- computer means, connected to receive the output signals of said light measuring devices, for the real-time calculation of population flash dynamics for the bioluminescent organisms in the seawater flowing through the detector chamber.

7. A system, as described in claim 1, wherein said light sensing means comprises a light measuring device which is flush-mounted in the detector chamber wall in close proximity to the detector chamber outlet, for generating a signal proportional to the light emitted by bioluminescent organisms in the seawater flowing through the detector chamber while the bioluminescent organisms are within the field of vision of the light measuring device, and said system further comprises pump control means, connected to receive the output signal of the light measuring device close to the detector chamber outlet, for adjusting the flow of seawater through the detector chamber to prevent light ejection from the detector chamber.

8. A system, as described in claim 1, wherein the hydrodynamic stimulus means comprises a grid having a distance between centers in the range of 1 to 3 centimeters, and a solidity in the range of 15% to 35%.

9. A system, as described in claim 1, which further comprises deployment means for raising and lowering the bioluminescence bathyphotometer in the ocean, at a controlled rate while maintaining the longitudinal axis of the bathyphotometer essentially horizontal.

10. A vertical profiling oceanic survey system, including a bioluminescence bathyphotometer which comprises:
- a longitudinal axis;
- a tubular detector chamber extending along the axis between an inlet end and an opposite outlet end of the chamber;
- pumping means, disposed adjacent the detector chamber outlet, for drawing seawater through the detector chamber at a selected rate of flow;
- a calibrated hydromechanical stimulus means, disposed adjacent the detector chamber inlet, for generating a defined turbulence field at the detector chamber inlet to stimulate bioluminescent plankton in the seawater flowing therethrough to generate light;
- flowmeter means for measuring the flow rate of seawater through the bathyphotometer; and
- light sensing means for sensing light emitted by bioluminescent plankton in the seawater flowing through the detector chamber, wherein said light sensing means includes
  - total light measuring means for measuring the total light produced by bioluminescent plankton in the seawater flowing through the detector chamber during the residence time of the plankton within the detector chamber, and
  - light flash counting means for counting the light flashes within the detector chamber produced by bioluminescent plankton excited by said stimulus means.

11. A system, as described in claim 10, wherein said light sensing means comprises:
- a plurality of light measuring devices which are evenly distributed along the length of the detector chamber and are flushmounted in the detector chamber wall, each light measuring device generating a signal proportional to the light emitted by bioluminescent organisms in the seawater flowing through the detector chamber while the bioluminescent organisms are within the field of vision of the light measuring device; and
- computer means, connected to receive the output signals of said light measuring devices, for the real-time calculation of population flash dynamics for the bioluminescent organisms in the seawater flowing through the detector chamber.

12. A system, as described in claim 10, which further comprises deployment means for raising and lowering the bioluminescence bathyphotometer in the ocean, at a controlled rate while maintaining the longitudinal axis of the bathyphotometer essentially horizontal.

13. A vertical profiling oceanic survey system, including a bioluminescence bathyphotometer which comprises:

a longitudinal axis;

a tubular detector chamber extending along the axis between an inlet end and an opposite outlet end of the chamber;

pumping means, disposed adjacent the detector chamber outlet, for drawing seawater through the detector chamber at a selected rate of flow;

a calibrated hydromechanical stimulus means, disposed adjacent the detector chamber inlet, for generating a defined turbulence field at the detector chamber inlet to stimulate bioluminescent plankton in the seawater flowing therethrough to generate light;

light sensing means for sensing light emitted by bioluminescent plankton in the seawater flowing through the detector chamber; and light blocking means for preventing the entrance of external light into the detector chamber, said light blocking means including a helical light baffle assembly adjacent to and upstream from the hydromechanical stimulus means, said helical light baffle including an open-ended cylindrical side wall affixed to said stimulus means and disposed concentrically about the axis, an axially-extending support spindle affixed at one end to the stimulus means and disposed concentrically within said cylindrical side wall, the free end of said spindle carrying a freely pivotable single ball bearing, and a rotor of lightweight non-reflecting material, including a cylindrical center portion having a rear axial bore into which the free end of said spindle extends, and having a helical flight extending for at least one turn about said center portion, the rear axial bore of the center portion extending to a radially-extending flat surface which is held in contact with said ball bearing whenever seawater is drawn through the detector chamber by the pumping means, as the rotor freely rotates about the axis.

14. A system, as described in claim 1, wherein the bioluminescence bathyphotometer further comprises intake means for maintaining laminar flow of seawater into and through the bathyphotometer until the onset of turbulence at the calibrated hydromechanical stimulus means, the intake means including an entry cone for maintaining an initial laminar flow and effecting the transition from zero to maximum flow of the entering seawater with minimum turbulence.

15. A system, as described in claim 14, wherein the bathyphotometer intake means further comprises light blocking means for preventing the entrance of external light into the detector chamber.

16. A system, as described in claim 10, wherein the bioluminescence bathyphotometer further comprises intake means for maintaining laminar flow of seawater into and through the bathyphotometer until the onset of turbulence at the calibrated hydromechanical stimulus means, the intake means including an entry cone for maintaining an initial laminar flow and effecting the transition from zero to maximum flow of the entering seawater with minimum turbulence.

17. A system, a described in claim 16, wherein the bathyphotometer intake means further comprises light blocking means for preventing the entrance of external light into the detector chamber.

18. A system, as described in claim 1, wherein the tubular detector chamber has a capacity of 16 liters.

19. A system, as described in claim 10, wherein said light sensing means comprises a light measuring device which is flush-mounted in the detector chamber wall in close proximity to the detector chamber outlet, for generating a signal proportional to the light emitted by bioluminescent organisms in the seawater flowing through the detector chamber while the bioluminescent organisms are within the field of vision of the light measuring device, and said system further comprises pump control means, connected to receive the output signal of the light measuring device close to the detector chamber outlet, for adjusting the flow of seawater through the detector chamber to prevent light ejection from the detector chamber.

* * * * *